(12) United States Patent
Laghi

(10) Patent No.: US 6,740,124 B1
(45) Date of Patent: May 25, 2004

(54) COSMETIC COVERS FOR PROSTHETIC LIMBS

(76) Inventor: Aldo A. Laghi, 14410 Eagle Point Dr., Clearwater, FL (US) 33762

( * ) Notice: Subject to any disclaimer, the term of this patent is extended or adjusted under 35 U.S.C. 154(b) by 51 days.

(21) Appl. No.: 10/063,417

(22) Filed: Apr. 22, 2002

(51) Int. Cl.[7] ................................................. A61F 2/74
(52) U.S. Cl. ........................................................ 623/27
(58) Field of Search ...................................... 623/27–56

(56) References Cited

U.S. PATENT DOCUMENTS

| | | | | |
|---|---|---|---|---|
| 3,400,408 A | * | 9/1968 | Garcia | 623/43 |
| 5,133,775 A | * | 7/1992 | Chen | 623/27 |
| 5,219,364 A | * | 6/1993 | Lloyd | 623/66 |
| 5,226,918 A | * | 7/1993 | Silagy et al. | 623/32 |
| 5,376,127 A | * | 12/1994 | Swanson | 623/27 |
| 5,425,780 A | * | 6/1995 | Flatt et al. | 623/38 |
| 6,083,265 A | * | 7/2000 | Shorter et al. | 623/27 |

* cited by examiner

*Primary Examiner*—Alvin Stewart
(74) *Attorney, Agent, or Firm*—Ronald E. Smith; Smith & Hopen, P.A.

(57) ABSTRACT

An endoprosthesis for below knee amputations includes a socket, a foam-covered pylon, and a prosthetic foot. A prosthetic knee is added for above knee amputations. A plastic sleeve is formed, heated, and stretched until it has a size sufficient to ensleeve the endoprothesis. The plastic sleeve is maintained at that enlarged size and cooled so that the resulting sleeve is substantially inelastic and is adapted to receive the endoprosthesis. The plastic sleeve is heated in areas where it does not conform exactly to the endoprosthesis until it shrinks and conforms exactly to the endoprosthesis, including the contour of the foam-covered pylon. The plastic sleeve then reveals all of the structural details of the prosthetic foam but does not apply compressive force to the foam. Lines of demarcation therefore do not form at the locations where the foam meets the prosthetic socket, the prosthetic knee, or the prosthetic foot.

1 Claim, 5 Drawing Sheets

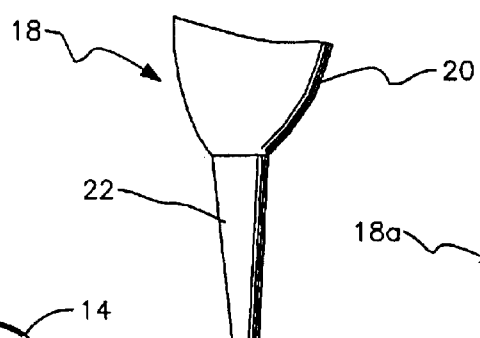
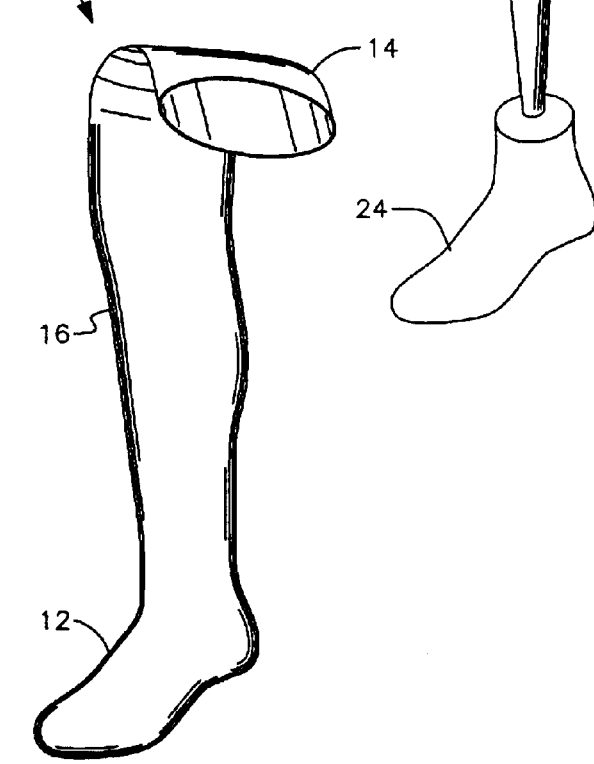
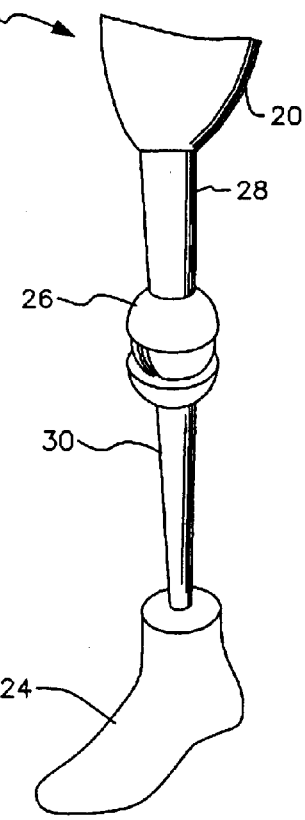

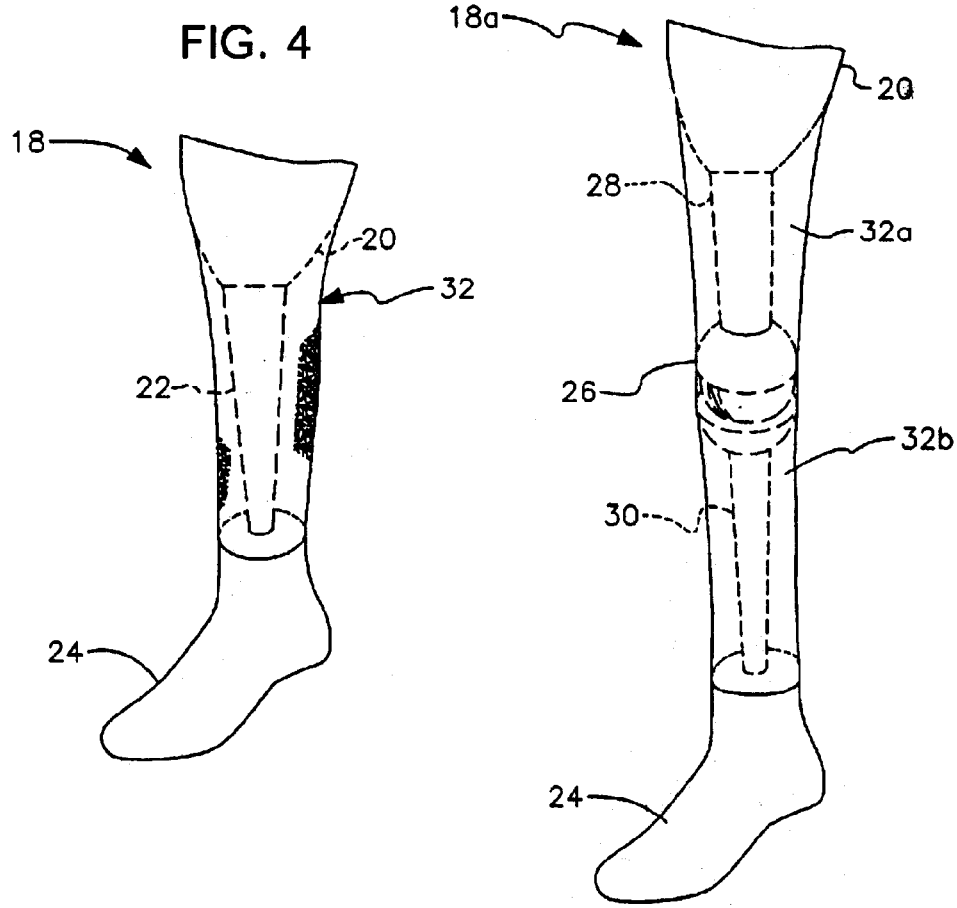

PRIOR ART

FIG. 8
FIG. 9
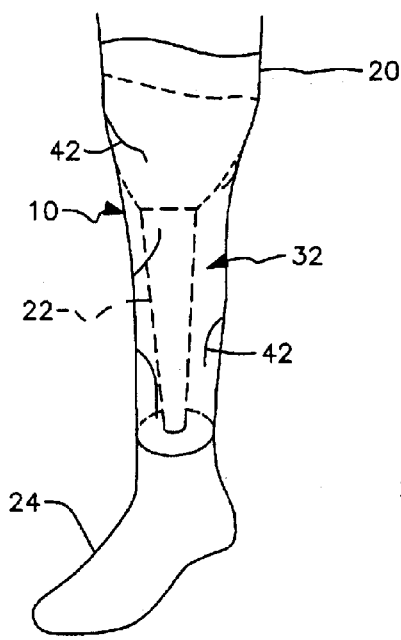
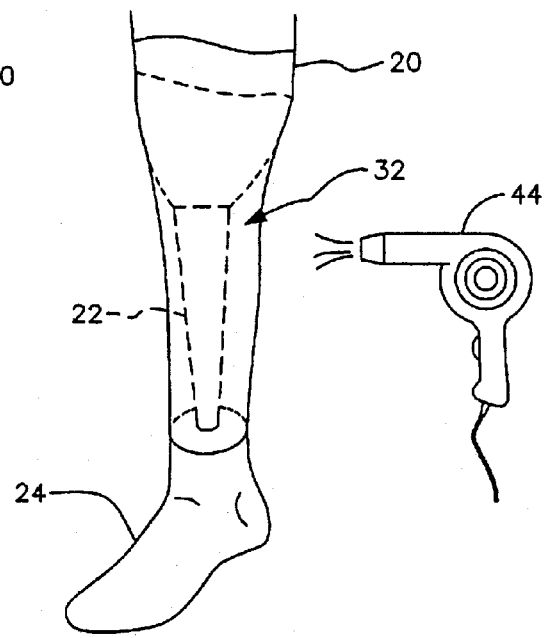

FIG. 10
FIG. 11
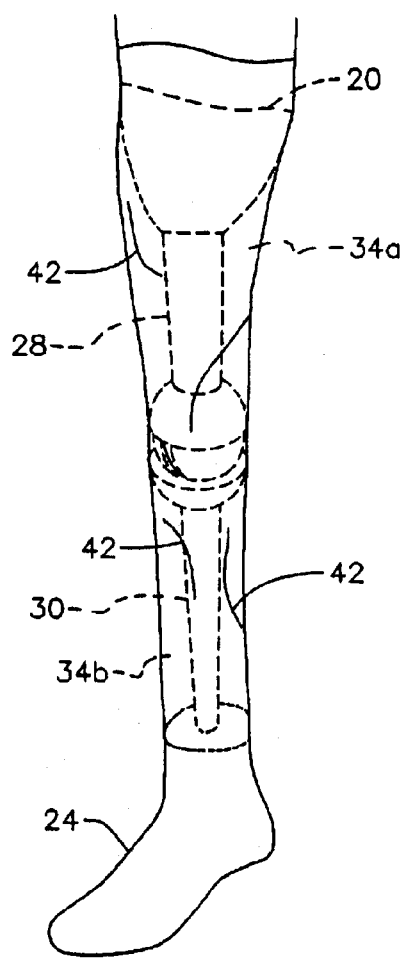
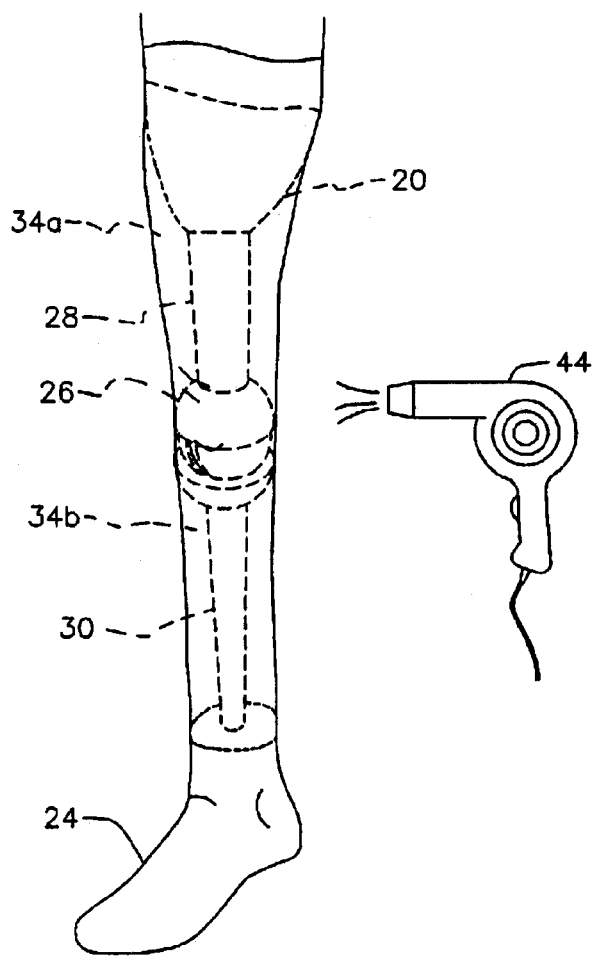

COSMETIC COVERS FOR PROSTHETIC LIMBS

BACKGROUND OF INVENTION

1. Field of the Invention

This invention relates, generally, to the art of prosthetics. More particularly, it relates to cosmetic covers for endoskeletal prostheses.

2. Description of the Prior Art

Exoskeletal prosthetic devices were in common use as recently as thirty (30) years ago. They are made of materials such as wood, fiberglass, or other suitable materials that may be shaped to approximate the appearance of a limb. The ability to provide the general appearance of a human limb is the primary advantage of an exoskeletal device.

Exoskeletal devices also have the advantage of being relatively easy to manufacture because they are made in one piece. Thus, they are weight-bearing and do not require supplementation with additional structural elements.

However, because an exoskeletal device is made in one piece, it cannot be adjusted as the user's gait changes and as the residual limb shrinks over time.

Endoskeletal prostheses have gradually supplanted exoskeletal devices during the last thirty years for several reasons. An endoskeletal device is stronger than an exoskeletal device of the same weight, and it can be adjusted over time as a user's gait changes and as a user's residual limb changes in size. The primary drawback of an endoskeletal prosthesis is that it has a functional, utilitarian or mechanical appearance and therefore bears little resemblance to the limb it replaces. For example, an endoskeletal prosthesis that performs the function of the tibia and Peron bones of a leg is provided in the form of straight pylon that does not resemble a human leg.

Moreover, endoskeletal prostheses are not one-piece structures. For a below knee amputee, an endoskeletal device will include a form-fitting socket for receiving a residual limb, a pylon that performs the function of the tibia and Peron bones in a human leg, a prosthetic foot that takes the reaction force from the ground and transmits it to the pylon and socket and ultimately to the bone structure of the amputee, and connection hardware that interconnects the various components. More particularly, connection hardware is required between the distal end of the socket and the proximal end of the pylon and between the distal end of the pylon and the proximal end of the prosthetic foot.

An above knee prosthesis requires all of the below-knee components, and a prosthetic knee joint as well. It provides angular motion similar to that of a human knee.

One advantage of having separate components is that a worn part may be replaced without replacing the entire prosthesis. An exoskeletal prosthesis, on the other hand, must be replaced in toto if any part thereof requires replacement.

Because endoskeletal prostheses are machine components with inadequate aesthetic value, the art has developed several techniques for covering the pylon with a cosmetic covering that approaches the appearance of a human limb. A common cosmetic covering is a foam known in the art as prosthetic foam. It can be shaped to substantially conform to the shape of a limb. Typically, the sound limb of an amputee is used as a model. The foam that covers the pylon is sculpted to look like the sound limb in shape and size. It is then spray painted with a flexible paint having a skin tone that matches the coloration of the sound leg. A skin tone stocking is then placed over the painted foam and a cosmetic cover is placed over the stocking. Depending upon the color of the cosmetic cover, it may or may not be painted. Thus, the cosmetic cover ensleeves the prosthetic foot, the foam-covered pylon, the prosthetic knee, and at least the distal end of the socket in above-knee amputation applications. In below knee applications where no prosthetic knee is required, the cosmetic cover ensleeves the prosthetic foot, the foam-covered pylon, and at least the distal end of the socket.

Two types of cosmetic covers have been developed for use with endoskeletal prostheses. Each of them has advantageous as well as disadvantageous properties.

The first type of cosmetic cover is substantially inelastic. Cosmetic covers exhibiting low elasticity are mass produced in many different sizes and shapes in the hope that a reasonable match may be found for each user. However, due to the wide variation in such parameters as ankle and calf geometry, both in circumference and longitudinal profile, a suitable match is seldom made between such an "off the shelf" product and the geometry of an amputee's limb. Moreover, due to the low elasticity of such a cover, it cannot conform to the surface details in the prosthetic foam that covers the pylon of an endoprosthetic device. A prosthetist may work diligently and with artistry to fashion a prosthetic foam cover that provides a good match to the amputee's sound limb, only to have the details of the prosthetic foam obliterated by an inelastic cosmetic cover that inadequately conforms to the realistic surfaces created by the prosthestist.

The second type of cosmetic cover has good elasticity characteristics and thus does not hide the work of the prosthetist. This type of cosmetic cover is desirable because it conforms exactly to the surface contour of the underlying prosthetic foam. Accordingly, the appearance of the prosthesis closely matches the appearance of the sound limb.

Highly elastic form-fitting cosmetic covers are thus initially more desirable than the inelastic type. Unfortunately, the bias provided by the elasticity continuously bears against the underlying prosthetic foam, applying a uniform pressure to it. After a few weeks or months, depending upon such factors as the stiffness of the foam and the elasticity of the cosmetic cover, the underlying foam sustains a set and shrinks. A uniform shrinkage in circumference is of little or no concern throughout most sections of the prosthesis, but in an above-knee prosthesis, it is problematic at the junction between the distal end of the prosthestic knee joint and the proximal end of the prosthetic foam, and the junction between the proximal end of the prosthetic foot and the distal end of the prosthetic foam. Neither the prosthetic knee joint nor the prosthetic foot are foam-covered so such parts do not undergo shrinkage. Thus, in above knee applications, a visible line of demarcation forms at the juncture between the prosthetic knee joint and the proximal end of the foam, and between the distal end of the foam and the prosthetic foot. In below knee applications, a visible line of demarcation forms at the juncture between the proximal end of the foam and the distal end of the socket and the distal end of the foam and the proximal end of the prosthetic foot. These lines of demarcation destroy the semblance of normalcy created by the careful sculpting and painting of the foam and the contour-following elasticity of the cosmetic cover.

Both types of cosmetic covers are thus understood to have significant drawbacks. What is needed is a cosmetic cover that provides the form-fitting benefits of a highly elastic cover without also causing the shrinkage of the underlying foam. The needed cosmetic cover would conform exactly to the underlying foam, as would a highly elastic cover, but would not apply a pressure thereto.

However, in view of the prior art considered as a whole at the time the present invention was made, it was not obvious to those of ordinary skill in the pertinent art how these inherently contradictory requirements could be fulfilled.

SUMMARY OF INVENTION

The long-standing but heretofore unfulfilled need for an improved cosmetic cover for an endoskeletal prosthesis is now met by a new, useful, and nonobvious invention. The invention provides a cosmetic cover that conforms precisely to the prosthetic foam it overlies without compressing the foam and causing development of lines of demarcation between foam-covered and non-foam-covered parts of the prosthesis.

The novel cosmetic cover of this invention includes a plastic sleeve having an elastic reinforced textile inside that has been pre-stretched so that it may be easily donned over a finished prosthesis and then heat shrunk into place. Different sections of the cosmetic cover are stretched by different percentages. A balloon, for comparison purposes, has a uniform thickness so that when it is inflated, all sections thereof are stretched by the same percentage. Thus, the geometry of an inflated balloon substantially matches the geometry of the balloon prior to inflation. The novel cosmetic cover of this invention, in contrast to a balloon, includes sections that are stretched to differing degrees.

The sections of the novel cosmetic cover that are subjected to more stress and wear during use are either: 1) made thicker; 2) made the same thickness but with fabric incorporated thereinto; or 3) made thicker and with fabric incorporated thereinto. In the first case, thicker sections of the plastic sleeve will stretch less than thinner sections thereof. In the second situation, the fabric is less elastic than the plastic sleeve so those sections of the plastic sleeve having fabric incorporated thereinto will stretch less than those sections of the plastic sleeve lacking fabric reinforcement. In the third scenario, the thicker sections of the plastic sleeve will also be fabric-reinforced so such sections will stretch less than sections that are thicker but not fabric reinforced or fabric reinforced but not thicker.

The ankle section and the foot section of a cosmetic cover are among the sections that are subjected to the greatest amount of wear and that therefore require greater thickness or fabric reinforcement, or both, to reduce their elasticity.

Some sections of a cosmetic cover should be pre-stretched to facilitate their donning over a completed prosthesis. Specifically, the ankle and foot sections should be larger when stretched to facilitate introduction of the prosthetic foot thereinto. Accordingly, when the novel cosmetic cover is pre-stretched, the ankle and foot sections thereof are stretched more than the other sections. Such stretching may be performed by inflating the cosmetic cover inside a preformed shell that constrains some sections against stretching but not other sections. The cosmetic cover is then heated, and cooled in the stretched form. It may also be performed mechanically by tensioning arms, in which case the cover is heated and cooled in the pre-stretched form.

The first cosmetic cover disclosed herein is used with an endoskeletal prosthesis of the type having utility in below knee amputations. The prosthesis includes a socket, a pylon, and a prosthetic foot. A pylon is covered with a prosthetic foam and the foam is contoured to match a contour of a sound limb. Areas of the plastic sleeve that do not conform to a contour of the prosthetic foam are shrunk by heating said areas until said areas conform to said contour. Alternatively, the cover can be shrunk to size by placing the whole prosthesis in an oven for a few minutes. When the heat source is removed, the substantially inelastic plastic sleeve does not exert enough pressure upon the prosthetic foam to cause it to compress. Therefore, no visible lines of demarcation form between the prosthetic foot and the distal end of the foam-covered pylon and no visible lines of demarcation form between the proximal end of the foam-covered pylon and the socket.

The second cosmetic cover disclosed herein is used with an endoskeletal prosthesis of the type having utility in above knee amputations. The prosthesis includes a socket, an upper pylon, a prosthetic knee, a lower pylon, and a prosthetic foot.

The upper pylon, the knee joint, and the lower pylon are covered with a prosthetic foam and the foam is contoured to match a contour of a sound limb. The cosmetic cover is placed into ensleeving relation to the prosthetic foot, the lower pylon, the prosthetic knee, the upper pylon, and the socket.

Areas of the plastic sleeve that do not conform to a contour of the prosthetic foam are shrunk by heating until said areas conform to said contour. Alternatively, the cover can be shrunk to size by placing the whole prosthesis in an oven for a few minutes. When the heat source is removed, the substantially inelastic plastic sleeve does not exert sufficient pressure upon the prosthetic foam to cause it to compress. Therefore, no visible lines of demarcation form between the distal end of the socket and a proximal end of the upper pylon-covering prosthetic foam. Nor do any visible lines of demarcation form the distal end of the prosthetic foam and the proximal end of the prosthetic foot.

An important object of this invention is to provide a cosmetic cover that overlies an endoskeletal prosthesis that includes prosthetic foam-covered parts and that conforms exactly to the contour of said foam to show all of the structural details thereof.

Another important object is to provide a cosmetic cover that does not compress the prosthetic foam that it overlies.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF DRAWINGS

For a fuller understanding of the nature and objects of the invention, reference should be made to the following detailed description, taken in connection with the accompanying drawings, in which:

FIG. 1 is a perspective view of a cosmetic cover made in accordance with the teachings of this invention;

FIG. 2 is a diagrammatic view of an endoskeletal prosthesis for use in a below knee amputation;

FIG. 3 is a diagrammatic view of an endoskeletal prosthesis for use in an above knee amputation;

FIG. 4 is a diagrammatic view depicting the endoskeletal prosthesis of FIG. 2 after the pylon thereof has been covered with a prosthetic foam that has been shaped to match the sound leg of a user;

FIG. 5 is a diagrammatic view depicting the endoskeletal prosthesis of FIG. 3 after the upper and lower pylons thereof have been covered with prosthetic foam that has been shaped to match the sound leg of a user;

FIG. 8 is a diagrammatic view of the endoskeletal prosthesis of FIG. 4 after it is covered by the novel cosmetic cover but before the novel cosmetic cover has been heat-treated;

FIG. 9 is a diagrammatic view of the endoskeletal prosthesis of FIG. 8 after the novel cosmetic cover has been heat-treated;

FIG. 10 is a diagrammatic view depicting the endoskeletal prosthesis of FIG. 5 after the prosthetic foam has been covered with the novel prosthetic cover of this invention; and FIG. 11 is a diagrammatic view depicting the endoskeletal prosthesis of FIG. 10 after the prosthetic foam has been covered with the novel prosthetic cover of this invention.

DETAILED DESCRIPTION

Figure 6:
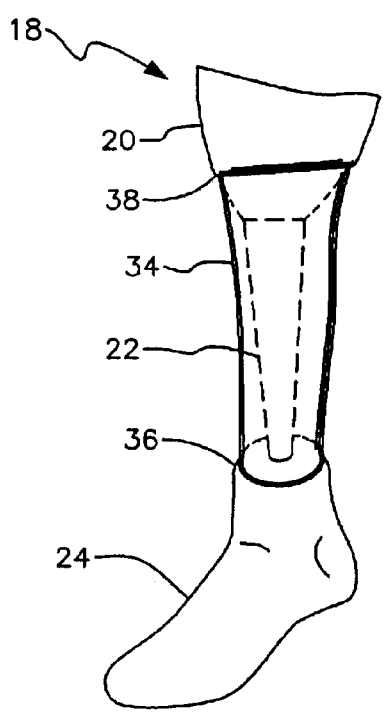
FIG. 6 is a diagrammatic view of a prior art below knee endoskeletal prosthesis after the foam-covered pylon thereof has been covered by an elastic cosmetic cover for a length of time sufficient to allow development of visible demarcation lines.

Referring to FIG. 1, it will there be seen that the reference numeral 10 denotes an illustrative embodiment of the novel cosmetic cover. It includes a distal end 12 that is adapted to cover a prosthetic foot, a proximal end 14 adapted to cover at least the distal end of a prosthetic socket, and a medial part 16 adapted to cover a pylon in below knee amputations. In above knee amputations it covers a prosthetic knee and upper (thigh) and lower (calf) pylons.

FIG. 2 depicts an endoskeletal prosthesis 18 that includes a socket 20 adapted to receive a residual limb, a pylon 22, and a prosthetic foot 24. When prosthesis 18 has been completed, only pylon 24 is covered with a prosthetic foam. Socket 20 and prosthetic foot 24 are not covered by said foam.

FIG. 3 depicts an endoskeletal prosthesis 18a that includes a socket 20 adapted to receive a residual limb, a prosthetic knee 26, an upper pylon 28, a lower pylon 30, and a prosthetic foot 26. It should be understood that only pylons 24 and 26 are covered with a prosthetic foam, i.e., socket 20, prosthetic knee 22, and prosthetic foot 26 are not covered by said foam.

FIG. 4 depicts endoskeletal prosthesis 18 of FIG. 2 after pylon 22 thereof has been covered in prosthetic foam 32. Note that socket 20 and prosthetic foot 24 are not covered by said foam.

FIG. 5 depicts endoskeletal prosthesis 18a of FIG. 3 after upper pylon 28 and lower pylon 30 have been covered in prosthetic foam 32a, 32b. Note that socket 20 and prosthetic foot 24 are not covered by said foam.

FIG. 6 depicts a prior art below knee endoskeletal prosthesis after it has been covered by a prior art elastic cosmetic cover 34 for a length of time sufficient to allow development of visible demarcation line 36 at the juncture of the proximal end of prosthetic foot 24 and the distal end of foam 34 and visible demarcation line 38 at the juncture of the proximal end of foam 34 and the distal end of socket 20. The development of visible demarcation lines 36 and 38 clearly diminishes the aesthetic appeal of prosthesis 18.

Figure 7:
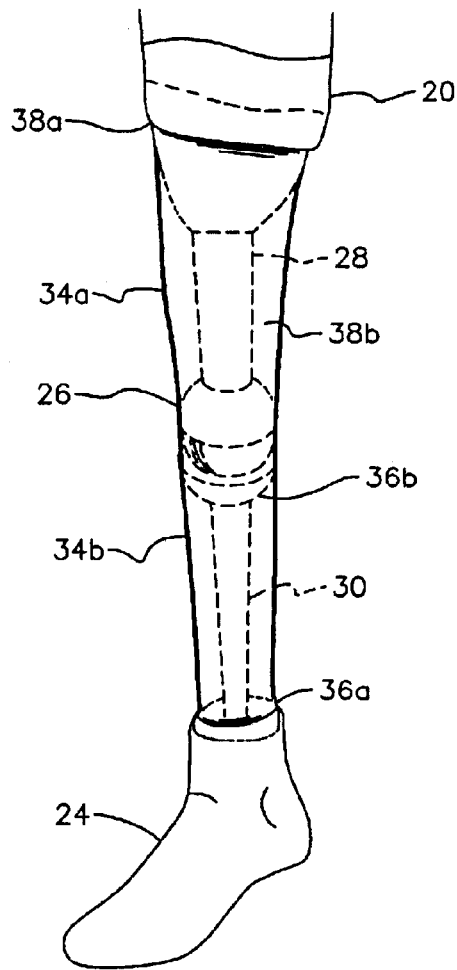
FIG. 7 is a diagrammatic view of a prior art above knee endoskeletal prosthesis after the foam-covered pylons thereof have been covered by an elastic cosmetic cover for a length of time sufficient to allow development of visible demarcation lines.

FIG. 7 depicts a prior art above knee endoskeletal prosthesis after upper pylon 28 has been covered by a prior art elastic cosmetic cover 34a for a length of time sufficient to allow development of visible demarcation line 36a at the juncture of prosthetic foot 24 and the distal end of foam 34b. Another visible demarcation line 38a is formed at the juncture of the proximal end of foam 34a and the distal end of socket 20. The development of visible demarcation lines 36a and 38a clearly diminish the aesthetic appeal of the prosthesis.

FIG. 8 depicts novel cosmetic cover 10 disposed in overlying relation to the endoskeletal prosthesis of FIG. 4. Wrinkle lines 42 are intended to convey the understanding that novel cosmetic cover 10 is not highly elastic and therefore does not conform tightly to prosthetic foam 32 when initially disposed in overlying relation thereto and therefore does not apply shrinkage-causing uniform pressure thereto.

FIG. 9 shows novel cosmetic cover 10 after the loose-fit represented by wrinkle lines 42 has been changed to a form-fitting fit. A suitable source of heat, represented here by a hand-held hot air blower 44, is used to heat novel cosmetic cover 10 at preselected areas until it shrinks in all heated areas and all wrinkle lines 42 are removed. The resulting fit conforms exactly to the contour of underlying prosthetic foam 32 and therefore reveals the details of the underlying prosthetic foam, just as if cosmetic cover 10 were of elastic construction, even though it is of relatively inelastic construction. Because novel cosmetic cover 10 is of substantially inelastic construction, it applies no inwardly-directed pressure to prosthetic foam 34. Said foam 34 therefore does not shrink with the passage of time and visible demarcation lines 36, 38 of the prior art do not appear.

FIG. 10 depicts novel cosmetic cover 10 disposed in overlying relation to the endoskeletal prosthesis of FIG. 5. Wrinkle lines 42 are intended to convey the understanding that novel cosmetic cover 10 is not highly elastic and therefore does not conform tightly to prosthetic foam 34 when initially disposed in overlying relation thereto and therefore does not apply shrinkage-causing uniform pressure thereto.

FIG. 11 shows novel cosmetic cover 10 after the loose-fit represented by wrinkle lines 42 has been changed to a form-fitting fit. A suitable source of heat, represented by a hand-held hot air blower 44, is used to heat novel cosmetic cover 10 at preselected areas until it shrinks in all heated areas and all wrinkle lines 42 are removed. The resulting fit conforms exactly to the contour of underlying prosthetic foam 34 and therefore reveals the details of the underlying prosthetic foam, just as if cosmetic cover 10 were of elastic construction, even though it is of relatively inelastic construction. Because novel cosmetic cover 10 is of substantially inelastic construction, it applies no inwardly-directed pressure to prosthetic foam 34. Said foam therefore does not shrink with the passage of time and visible demarcation lines 36 and 38 of the prior art (FIG. 7) do not appear.

Novel cosmetic cover 10 is formed of plastic that is molded at a small size and then pre-stretched to a larger size. FIG. 1 is intended to depict a cosmetic cover 10 after it has been heated and stretched. However, since the stretching is either uniform or preferential and the drawing is not to scale, FIG. 1 may also be interpreted as depicting the plastic cosmetic cover after it has been molded at a small size and before it has been heated and stretched uniformly to a larger size. After the stretching procedure is concluded, the stretched cosmetic cover is maintained at its larger size and cooled. It fits somewhat loosely over a wide range of sizes of endoskeletal prostheses, exhibiting wrinkle lines 42 as aforesaid. Significantly, many areas of cosmetic cover 10 fit precisely to the underlying endoskeletal prosthesis, including the prosthetic foam. Only those parts that are loose need to be heat-treated in the manner depicted in FIGS. 9 and 11.

Novel cosmetic cover 10 fits such a large range of sizes of endoskeletal prostheses that only one or two pre-stretched sizes is needed to fit almost all endoskeletal prostheses. The novel cosmetic cover thus provides the benefit of perfectly conforming to the underlying prosthetic foam so that no structural details are obliterated while providing no uniform pressure on the underlying foam and therefore developing no demarcation lines of the type present in prior art endoprostheses.

The invention has similar utility in the construction of endoprosthetic arms. For example, if used in prosthetic arm construction, it would prevent formation of visible lines of demarcation at the juncture of a prosthetic wrist and the distal end of a foam-covered forearm pylon and at the juncture of the proximal end of the foam-covered forearm pylon and a prosthetic elbow, for example.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described,

What is claimed is:

1. A cosmetic cover for an endoskeletal prosthesis, comprising:

a substantially inelastic plastic sleeve;

said plastic sleeve being pre-stretched to a shape that resembles a human leg;

said plastic sleeve loosely ensleeving a prosthetic foot, a foam-covered pylon, and a prosthetic socket;

said plastic sleeve being formed of a heat-shrinkable plastic that shrinks in response to application of heat and conforms to the shape of said prosthetic foot, said foam-covered pylon, and said prosthetic socket;

said plastic sleeve when cooled being substantially inelastic;

said substantially inelastic plastic sleeve not exerting a uniform pressure upon said prosthetic foam;

no visible lines of demarcation being formed between said prosthetic foot and a distal end of said foam-covered pylon; and no visible lines of demarcation being formed between a proximal end of said foam-covered pylon and said prosthetic socket.

* * * * *